United States Patent [19] [11] 4,306,900
Swithenbank et al. [45] Dec. 22, 1981

[54] HERBICIDAL NITRODIPHENYL ETHERS

[75] Inventors: Colin Swithenbank, Perkasie; Ted Fujimoto, Warminster, both of Pa.

[73] Assignee: Rohm and Haas Company, Philadelphia, Pa.

[21] Appl. No.: 182,372

[22] Filed: Aug. 29, 1980

Related U.S. Application Data

[62] Division of Ser. No. 17,869, Mar. 5, 1979, abandoned.

[51] Int. Cl.³ .................. A01N 31/14; C07C 49/84
[52] U.S. Cl. ................................. 71/123; 71/105; 71/122; 568/306; 568/586
[58] Field of Search ................... 71/105, 123; 568/306

[56] References Cited

U.S. PATENT DOCUMENTS 3,423,470 1/1969 Rohr et al. ........................ 568/306
3,776,961 12/1973 Theissen ............................ 71/123
3,928,416 12/1975 Bayer et al. ....................... 71/105

Primary Examiner—Paul M. Coughlan, Jr.
Attorney, Agent, or Firm—Terence P. Strobaugh; George W. Simmons

[57] ABSTRACT

Compounds of the formula

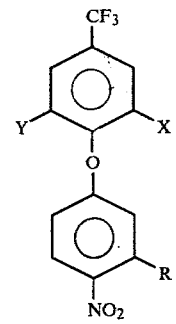

wherein
X is a hydrogen atom, a halogen atom, a trihalomethyl group, an alkyl group, or a cyano group;
Y is a hydrogen atom or a halogen atom;
R is CHOHR' or COR'; and
R' is hydrogen or ($C_1$–$C_4$)alkyl;

and compositions containing these compounds which exhibit herbicidal activity.

15 Claims, No Drawings

HERBICIDAL NITRODIPHENYL ETHERS

This is a division of application Ser. No. 17,869 filed Mar. 5, 1979, now abandoned.

This invention relates to novel compounds which show activity as herbicides, to novel herbicidal compositions which contain these compounds, and to new methods of controlling weeds with these herbicidal compositions.

Certain diphenyl ethers have been shown to be effective weed control agents. However, the herbicidal effectiveness of a given diphenyl ether cannot be predicted from an examination of the substituent groups attached to the phenyl rings in the ether, and often quite closely related compounds will have quite different weed control abilities. Various diphenyl ethers may have overlapping or complementary areas of activity or selectivity, and can thus be useful in combination to control a variety of weeds upon application of a single composition.

An ideal herbicide should give selective weed control, over the full growing season, with a single administration at low rates of application. It should be able to control all common weeds by killing them as the seed, the germinating seed, the seedling, and the growing plant. At the same time, the herbicide should not be phytotoxic to the crops to which it is applied and should decompose or otherwise be dissipated so as not to poison the soil permanently. The known diphenyl ether herbicides often fall short of these ideals, and it would thus be desirable to have new herbicides which show even more selective control of undesirable plants among desirable crop plants or which complement the known diphenyl ethers in activity.

In accordance with the present invention, there is provided a class of diphenyl ethers having the formula

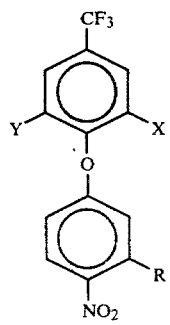

wherein
- X is a hydrogen atom, a halogen atom, preferably a fluorine atom or a chlorine atom; a trihalomethyl group, preferably a trifluoromethyl group; or a (C$_1$–C$_4$)alkyl group, preferably a methyl group, or a cyano group;
- Y is a hydrogen atom or a halogen atom, preferably a fluorine atom or a chlorine atom.
- R is a CHOHR' group or a COR' group; and
- R' is a hydrogen atom or a (C$_1$–C$_4$)alkyl group preferably a methyl group.

Particular preferred compounds of the invention have the following formulas:

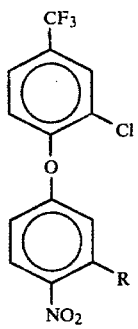

wherein
- R$_1$ is COR'; and R$^1$
- R$^1$ is a hydrogen atom, a methyl group or an ethyl group;

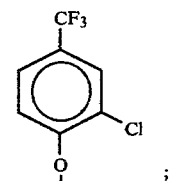

;

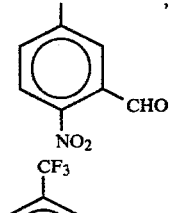

;

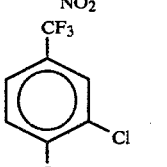

; and

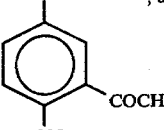

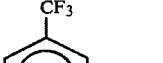

;

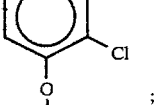

These compounds have been found to show activity as weed control agents. In a preferred embodiment of the invention, X is a chlorine atom, Y is a hydrogen atom and R is a COR' group.

Examples of the compounds of the invention embraced by Formula I include:
2-fluoro-4-trifluoromethyl-3'-n-butylcarbonyl-4'-diphenylether
2,6-difluoro-4-trifluoromethyl-3'-i-propylcarbonyl-4'-diphenylether 2-fluoro-6-chloro-4-trifluoromethyl-3'-formyl-4'-nitrodiphenylether 2-cyano-4-trifluoromethyl-3'-(1-hydroxy-n-butyl)-4'-nitrodiphenylether 2,4-bis(trifluoromethyl)-3'-ethylcarbonyl-4'-nitrodiphenylether The novel diphenyl ethers of the invention are useful both as preemergence and as postemergence herbicides. Preemergence herbicides are ordinarily used to treat the soil in which the desired crop is to be planted by application either before seeding, during seeding, or, as in most applications, after seeding and before the crop emerges. Postemergence herbicides are those which are applied after the plants have emerged and during their growth period.

Among the crops on which the diphenyl ethers of the invention can be advantageously employed are, for example, cotton, soybeans, peanuts, safflower, beans, peas, carrots, corn, wheat, and other cereal groups.

Diphenyl ethers of the invention are useful for controlling weeds in rice crops. When used in transplanted rice crops, the ethers can be applied either preemergence or postemergence to the weeds—that is, they can be applied to the growth medium of the transplanted plants either before the weed plants have emerged or while they are in their early stages of growth. The ethers can be applied to the growth medium either before or after the rice has been transplanted to that medium.

The diphenyl ethers of the invention can be applied in any amount which will give the required control of weeds. A preferred rate of application of the herbicides of the invention is from about 0.1 to about 12, and most preferably about 0.25 to 4, pounds of the diphenyl ether per acre.

Under some conditions, the diphenyl ethers of the invention may be advantageously incorporated into the soil or other growth medium prior to planting a crop. This incorporation can be carried out by any convenient means, including by simple mixing with the soil, by applying the diphenyl ether to the surface of the soil and then disking or dragging into the soil to the desired depth, or by employing a liquid carrier to accomplish the necessary penetration and impregnation.

A diphenyl ether of the invention can be applied to the growth medium or to plants to be treated either by itself or, as is generally done, as a component in a herbicidal composition or formulation which also comprises an agronomically acceptable carrier. By agronomically acceptable carrier is meant any substance which can be used to dissolve, disperse, or diffuse a herbicidal compound in the composition without impairing the effectiveness of the herbicidal compound and which by itself has no detrimental effect on the soil, equipment, crops, or agronomic environment. Mixtures of the diphenyl ethers of the invention may also be used in any of these herbicidal formulations. The herbicidal composition of the invention can be either solid or liquid formulations or solutions. For example, the diphenyl ethers can be formulated as wettable powders, emulsifiable concentrates, dusts, granular formulations, aerosols, or flowable emulsion concentrations. In such formulations, the compounds are extended with a liquid or solid carrier and, when desired, suitable surfactants are incorporated.

It is usually desirable, particularly in postemergence applications, to include adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers Annual".

The diphenyl ether compounds of this invention can be dissolved in any appropriate solvent. Examples of solvents which are useful in the practice of this invention include alcohols, ketones, aromatic hydrocarbons, halogenated hydrocarbons, dimethylformamide, dioxane, dimethyl sulfoxide, and the like. Mixtures of these solvents can also be used. The concentration of the solution can vary from about 2% to about 98% with a preferred range being about 25% to about 75%.

For the preparation of emulsifiable concentrates, the diphenyl ether can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent which permits dispersion in water. Suitable emulsifiers include, for example, the ethylene oxide derivatives of alkylphenols or long-chain alcohols, mercaptans, carboxylic acids, and reactive amines and partially esterified polyhydric alcohols. Solvent-soluble sulfates or sulfonates, such as the alkaline earth salts or amine salts of alkylbenzenesulfonates and the fatty alcohol sodium sulfates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilizing agent such as a water-soluble cellulose derivative or a water-soluble salt of a polyacrylic acid. The concentration of the active ingredient in emulsifiable concentrates is usually about 10% to 60% and in flowable emulsion concentrates, this can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of about 20% to 98%, preferably about 40% to 75%. A dispersing agent can constitute about 0.5% to about 3% of the composition, and a wetting agent can constitute from about 0.1% to about 5% of the composition.

Dusts can be prepared by mixing the compounds of the invention with finely divided inert solids which may be organic or inorganic in nature. Materials useful for this purpose include, for example, botanical flours, silicas, silicates, carbonates and clays. One convenient method of preparing a dust is to dilute a wettable powder with a finely divided carrier. Dust concentrates containing about 20% to 80% of the active ingredient are commonly made and are subsequantly diluted to about 1% to 10% use concentration.

Granular formulations can be prepared by impregnating a solid such as granular fuller's earth, vermiculite, ground corn cobs, seed hulls, including bran or other grain-hulls, or similar material. A solution of one or more of the diphenyl ethers in a volatile organic solvent can be sprayed or mixed with the granular solid and the solvent then removed by evaporation. The granular material can have any suitable size, with a preferable size range of 16 to 20 mesh. The diphenyl ether will usually comprise about 2 to 15% of the granular formulation.

The diphenyl ethers of the invention can also be mixed with fertilizers or fertilizing materials before their application. In one type of solid fertilizing composition in which the diphenyl ethers can be used, particles of a fertilizer or fertilizing ingredients, such as ammonium sulfate, ammonium nitrate, or ammonium phosphate, can be coated with one or more of the ethers. The solid diphenyl ethers and solid fertilizing material can also be admixed in mixing or blending equipment, or they can be incorporated with fertilizers in granular formulations. Any relative proportion of diphenyl ether and fertilizer can be used which is suitable for the crops and weeds to be treated. The diphenyl ether will commonly be from about 5% to about 25% of the fertilizing composition. These compositions provide fertilizing materials which promote the rapid growth of desired plants, and at the same time control the growth of undesired plants.

The diphenyl ethers of the invention can be applied as herbicidal sprays by methods commonly employed, such as conventional high-gallonage hydraulic sprays, low gallonage sprays, airblast spray, aerial sprays and dusts. For low volume applications a solution of the compound is usually used. The dilution and rate of application will usually depend upon such factors as the type of equipment employed, the method of application, the area to be treated and the type and stage of development of the weeds.

For some applications, it may be desirable to add one or more other herbicides along with diphenyl ethers of the invention. Examples of other herbicides which can be incorporated to provide additional advantages and effectiveness include:

Carboxylic Acids and Derivatives 2,3,6-trichlorobenzoic acid and its salts
2,3,5,6-tetrachlorobenzoic acid and its salts
2-methoxy-3,5,6-trichlorobenzoic acid and its salts
2-methoxy-3,6-dichlorobenzoic acid and its salts
2-methyl-3,6-dichlorobenzoic acid and its salts
2,3-dichloro-6-methylbenzoic acid and its salts
2,4-dichlorophenoxyacetic acid and its salts and esters
2,4,5-trichlorophenoxyacetic acid and its salts and esters
2-methyl-4-chlorophenoxyacetic acid and its salts and esters
2-(2,4,5-trichlorophenoxy)propionic acid and its salts and esters
4-(2,4-dichlorophenoxy)butyric acid and its salts and esters
4-(2-methyl-4-chlorophenoxy)butyric acid and its salts and esters
2,3,6-trichlorophenylacetic acid and its salts
3,6-endoxohexahydrophthalic acid
dimethyl 2,3,5,6-tetrachloroterephthalate
trichloracetic acid and its salts
2,2-dichloropropionic acid and its salts
2,3-dichloroisobutyric acid and its salts

Carbamic Acid Derivatives ethyl N,N-di(n-propyl)thiolcarbamate
propyl N,N-di(n-propyl)thiolcarbamate
ethyl N-ethyl-N-(n-butyl)thiolcarbamate
propyl N-ethyl-N-(n-butyl)thiolcarbamate
2-chlorallyl N,N-diethyldithiocarbamate
N-methyldithiocarbamic acid salts
ethyl 1-hexamethyleneiminecarbothiolate
isopropyl N-phenylcarbamate
isopropyl N-(m-chlorophenyl)carbamate
4-chloro-2-butynyl N-(m-chlorophenyl)carbamate
methyl N-(3,4-dichlorophenyl)carbamate

Phenols dinitro-o-(sec-butyl)phenol and its salts
pentachlorophenol and its salts

Substituted Ureas 3-(3,4-dichlorophenyl)-1,1-dimethylurea
3-phenyl-1,1-dimethylurea
3-(3,4-dichlorophenyl)-3-methoxy-1,1-dimethylurea
3-(4-chlorophenyl)-3-methoxy-1,1-dimethylurea
3-(3,4-dichlorophenyl)-1-n-butyl-1-methylurea
3-(3,4-dichlorophenyl)-1-methoxy-1-methylurea
3-(4-dichlorophenyl)-1-methoxy-1-methylurea
3-(3,4-dichlorophenyl)-1,1,3-trimethylurea
3-(3,4-dichlorophenyl)-1,1-diethylurea
dichloral urea

Substituted Triazines 2-chloro-4,6-bis(ethylamino)-s-triazine
2-chloro-4-ethylamino-6-isopropylamino-s-triazine
2-chloro-4,6-bis(methoxypropylamino)-s-triazine
2-methoxy-4,6-bis(isopropylamino)-s-triazine
2-chloro-4-ethylamino-6-(3-methoxypropylamino)-s-triazine
2-methylmercapto-4,6-bis(isopropylamino)-s-triazine
2-methylmercapto-4,6-bis(ethylamino)-s-triazine
2-methylmercapto-4-ethylamino-6-isopropylamino-s-triazine
2-chloro-4,6-bis(isopropylamino)-s-triazine
2-methoxy-4,6-bis(ethylamino)-s-triazine
2-methoxy-4-ethylamino-6-isopropylamino-s-triazine
2-methylmercapto-4-(2-methoxyethylamino)-6-isopropylamino-s-triazine

Diphenyl Ether Derivatives 2,4-dichloro-4'-nitrodiphenyl ether
2,4,6-trichloro-4'-nitrodiphenyl ether
2,4-dichloro-6-fluoro-4'-nitrodiphenyl ether
3-methyl-4'-nitrodiphenyl ether
3,5-dimethyl-4'-nitrodiphenyl ether
2,4-dinitro-4-trifluoromethyldiphenyl ether
2,4-dichloro-3'-methoxy-4'-nitrodiphenyl ether

Anilides

N-(3,4-dichlorophenyl)propionamide
N-(3,4-dichlorophenyl)methacrylamide
N-(3-chloro-4-methylphenyl)-2-methylpentanamide
N-(3,4-dichlorophenyl)trimethylacetamide
N-(3,4-dichlorophenyl)-$\alpha,\alpha$-dimethylvaleramide
N-isopropyl-N-phenylchloroacetamide
N-n-butoxymethyl-N-(2,6-diethylphenyl)chloroacetamide
N-n-methoxymethyl-N-(2,6-diethylphenyl)chloroacetamide

Uracils 5-bromo-3-s-butyl-6-methyluracil
5-bromo-3-cyclohexyl-1,6-dimethyluracil
3-cyclohexyl-5,6-trimethyleneuracil
5-bromo-3-isopropyl-6-methyluracil
3-tert-butyl-5-chloro-6-methyluracil

Nitriles 2,6-dichlorobenzonitrile diphenylacetonitrile
3,5-dibromo-4-hydroxybenzonitrile
3,5-diiodo-4-hydroxybenzonitrile Other Organic Herbicides 2-chloro-N,N-diallylacetamide
N-(1,1-dimethyl-2-propynyl)-3,5-dichlorobenzamide
maleic hydrazide
3-amino-1,2,4-triazole
monosodium methanearsonate
disodium methanearsonate
N,N-dimethyl-α,α-diphenylacetamide
N,N-di(n-propyl)-2,6-dinitro-4-trifluoromethylaniline
N,N-di(n-propyl)-2,6-dinitro-4-methylaniline
N,N-di(n-propyl)-2,6-dinitro-4-methylsulfonylaniline
Dimethyl 4,4'-bipyridylium dichloride
0-(2,4-dichlorophenyl)-0-methyl-isopropylphosphoramidothioate
4-amino-3,5,6-trichloropicolinic acid
2,3-dichloro-1,4-naphthoquinone
di(methoxythiocarbonyl)disulfide
3-isopropyl-1H-2,1,3-benzothiadiazine-(4)3H-one-2,2-dioxide
1,1'-dimethyl-4,4'-bipyridinium salts
3,4,5,6-tetrahydro-3,5-dimethyl-2-thio-2H-1,3,5-thiadiazine.

When mixtures of herbicides are employed, the relative proportions which are used will depend upon the crop to be treated and the degree of selectivity in weed control which is desired.

The diphenyl ethers of the invention or their precursors can be prepared by reacting a suitably substituted phenol, or the potassium or sodium salt of the phenol, with a suitably substituted halobenzene, such as a chloro- or fluorobenzene, in the presence of an alkaline agent.

More specific synthesis are described below:

SYNTHESIS 1

Aldehydes of the invention may be prepared by hydrolysis of the corresponding benzal halides, in turn prepared by free radical halogenation of the toluene. Catalytic methods are available for direct oxidation of the toluene to aldehyde. They may also be prepared by the controlled oxidation of the corresponding carbinol or controlled reduction of the acid or acid derivatives of like esters. Oxidation of the amino-methyl, or chloromethyl derivatives will also yield the aldehyde, as will controlled reduction of the nitrile followed by hydrolysis of the intermediate imine. In most cases, introduction of the nitro group takes place after formation of the aldehyde.

SYNTHESIS 2

Carbinols of the inventon may be prepared from the corresponding esters or other acid derivatives, or ketones, by reduction, for example with metal hydrides, or from the aldehyde by reaction with a metal alkyl, e.g. an alkyl lithium, or Grignard reagent. They may also be prepared from the corresponding alkyl benzene either directly, by controlled oxidation, or by controlled monohalogenation followed by hydrolysis. Again, nitration will take place either before or after construction of the side chain.

SYNTHESIS 3

Alkylketones may be prepared by the reaction of the corresponding nitrile with a metal alkyl reagent followed by the hydrolysis of the intermediate imine, or by a carefully controlled reaction with suitable esters, for which the cadmium alkyls may be preferred. Oxidation of the corresponding alkylbenzenes or carbinols will also yield ketones, the formr including oxidations by halogens. Again, nitration may take place either before or after construction of the side chain.

Alternatively, the side chain may be introduced before construction of the diphenylether. For example, the potassium salt of m-acetylphenol may be condensed with 3,4-dichlorobenzotrifluoride to give a diphenylether which on nitration yields 2-chloro-4-trifluoromethyl-3'-acetyl-4'-nitrodiphenylether.

The following examples will further illustrate this invention but are not intended to limit it in any way.

EXAMPLE 1

Preparation of 2-chloro-4-trifluoromethyl-3'-hydroxymethyl-4'-nitrodiphenylether A solution of 2-chloro-4-trifluoromethyl-3'-carbomethoxy-4'-nitrodiphenylether (1.5 g) in tetrahydrofuran (20 ml) at −10° C. is treated with lithium aluminum hydride (400 mg) added in one lot. The reaction exotherms to +10° C. and after 60 seconds is quenched by pouring onto ice/water. This reaction is repeated five times and the combined products diluted with ether, washed with water, dried, stripped, filtered through silica gel in 50% benzene/hexane, stripped and recrystallized from hexane to give the carbinol (3 g) m.p. 88°–91° C.

EXAMPLE 2

2-Chloro-4-trifluoromethyl-3'-ethyl-carbonyldiphenylether

A solution of potassium hydroxide (6.5 g 85% pure, 0.99 more) in water (20 ml) is added to a solution of 3-hydroxypropiophenone (14.26 g, 0.95 mole) in sulpholane (150 ml) and toluene (80 ml), and the mixture heated under reflux on a Dean and Stark apparatus until no more water is collected. The toluene is then stripped off and 3,4-dichlorobenzotrifluoride added at 135° C. slowly dropwise, then heaed at 135°–140° C. for six hours. The mixture is cooled, diluted with water, and extracted with pentane. The extract is filtered through silica gel and stripped to give ethylcarbonyl diphenylether, yield 14.6 g.

EXAMPLE 3

2-Chloro-4-trifluoromethyl-3'-ethylcarbonyl-4'-nitrodiphenylether

Concentrated nitric acid (5.0 g) is added slowly dropwise to a solution of 2-chloro-4-trifluoromethyl-3'-ethylcarbonyldiphenylether (10 g) in acetic anhydride (35 ml) and sulphuric acid (100 mg) at 10° C. and the mixture allowed to warm to room temperature. After 30 minutes, the mixture is poured onto ice and extracted with ether and the extract washed with sodium bicarbonte solution, dried, filtered through silica gel and stripped to give 2-chloro-4-trifluoromethyl-3'-ethylcarbonyl-4'-nitrodiphenylether, 9.84 g as a golden oil.

EXAMPLE 4

2-Chloro-4-trifluoromethyl-3'-formyl4'-nitrodiphenylether 2-chloro-4-trifluoromethylphenol 4.63 g (0.0236 mol) 3.26 g (0.0236 mol) $K_2CO_3$ and 4.0 g (0.023 mol) of 2-nitro-5-fluorobenzaldehyde are mixed in 25 ml DMSO at room temperature. After stirring at room temperature for 101 hrs, the reaction is diluted with water and extracted into benzene. The benzene layer is dried over $MgSO_4$ and stripped yielding a yellow solid. The solid is recrystallized from benzene-pentane. M.P. 99° C. yield 5.5 g (69%).

In Table I, typical diphenyl ethers of the invention are listed with their melting points and elemental analysis.

Table II shows the herbicidal activity of the diphenyl ethers of the invention towards a number of common weeds. Using the procedure described below, diphenyl ethers were evaluated for control of the following weeds:

Monocots barnyardgrass (*Echinochloa crusgalli*)
downy brome (*Bromus tectorum*)
green foxtail (*Setaria viridis*)
johnsongrass (*Sorghum halopense*)
yellow nutsedge (*Cyperus esculentus*)
wild oats (*Avena fatua*)

Dicots cocklebur (*Xanthium pensylvanicum*)
marigold (*Tagetes patula*)
morningglory (*Ipomoea purpurea*)
nightshade (*Solanum nigrum*)
safflower (*Carthamus tinctorius*)
tomato (*Eycopersicon esculentum*)
velvetleaf (*Abutilon theophrasti*)

The following test procedure is employed. Seeds of selected crops and weeds are plants in soil in flats. For preemergence tests, the flats are treated with the test compound immediately after the planting. For postemergence tests, the seeds are allowed to germinate, and after two weeks the flats are treated with the test compound. The compound to be evaluated is dissolved in acetone, diluted with water, and sprayed over the flats using a carrier volume equivalent to 50 gallons per acre at the rate of application (pounds per acre, lb/A.) specified in the table. About two weeks after the application of the test compound, the state of growth of the plants is observed and the phytotoxic effect of the compound is evaluated. Table II gives the average percentage control achieved by the test compounds in terms of the percent of the plants which are killed by the compounds.

TABLE 1

Elemental Analysis

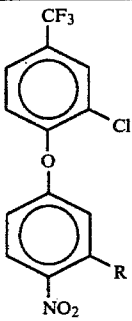

| Compound | R | | | % C | % H | % N | % Cl | % F |
|---|---|---|---|---|---|---|---|---|
| 1. | $CH_2OH$ | $C_{14}H_9ClF_3NO_4$ | Found | 48.39 | 2.62 | 3.78 | 10.34 | 15.89 |
| | m.p. 8-91° C. | | reqs. | 48.36 | 2.61 | 4.03 | 10.20 | 16.39 |
| 2. | CHOCEt. | $C_{16}H_{13}ClF_3NO_4$ | Found | 51.40 | 3.59 | 3.34 | 9.63 | |
| | oil | | reqs. | 51.1 | 3.5 | 3.7 | 9.4 | |
| 3. | CHO | $C_{14}H_7ClF_3NO_4$ | Found | 48.51 | 2.02 | 3.95 | 10.39 | 16.77 |
| | m.p. 99° C. | | reqs. | 48.65 | 2.04 | 405 | 10.26 | 16.49 |
| 4. | COMe | $C_{15}H_9ClF_3NO_4$ | Found | 49.78 | 2.49 | 4.17 | 9.67 | |
| | m.p. 83-85° C. | | reqs. | 50.09 | 2.52 | 3.89 | 19.86 | |
| 5. | COEt | $C_{16}H_{11}ClF_3NO_4$ | Found | 51.77 | 2.96 | 4.28 | | 15.27 |
| | oil | | reqs. | 51.45 | 2.96 | 3.75 | | 15.25 |

TABLE II

Biological Data

| | | MONOCOTS | | | | | | DICOTS | | | | | | |
|---|---|---|---|---|---|---|---|---|---|---|---|---|---|---|
| Compound | lbs/A | Barnyardgrass | Downybrome | Green Foxtail | Johnsongrass (seedlings) | Yellow Nutsedge | Wild Oats | Cocklebur | Marigold | Tomato | Morningglory | Nightshade | Velvetleaf | Safflower |
| 1. | Pre 2 | 80 | 0 | 100 | — | 0 | 0 | 0 | 0 | 0 | 0 | — | 70 | — |
| | Post 4 | 30 | 0 | 30 | — | 0 | 20 | 0 | 20 | 30 | 50 | — | 70 | — |
| 2. | Pre 2 | 20 | 0 | 90 | — | 0 | 0 | — | 50 | 0 | 10 | — | 100 | — |
| | Pre 4 | 95 | 60 | 100 | — | 0 | 30 | — | 95 | 75 | 80 | — | 100 | — |
| | Post 2 | 0 | 0 | 10 | — | 0 | 20 | 10 | 0 | 0 | 10 | — | 70 | — |
| | Post 4 | 0 | 0 | 10 | — | 0 | 0 | 0 | 40 | 50 | 20 | — | 20 | — |
| 3. | Pre 4 | 90 | 80 | 100 | 100 | 80 | 20 | 0 | — | — | 100 | 50 | 80 | 30 |
| | Post 4 | 70 | 0 | 60 | 80 | 40 | 20 | 80 | — | — | 70 | 90 | 95 | 20 |
| 4. | Pre 2 | 100 | 99 | 100 | — | 80 | 99 | 70 | 100 | 100 | 100 | — | 100 | — |

TABLE II-continued

Biological Data

| | | MONOCOTS | | | | | | DICOTS | | | | | | |
|---|---|---|---|---|---|---|---|---|---|---|---|---|---|---|
| Compound | lbs/A | Barnyard-grass | Downy-brome | Green Foxtail | Johnson-grass (seedlings) | Yellow Nuts-edge | Wild Oats | Cockel-bur | Mari-gold | To-mato | Morning-glory | Night-shade | Velvet-leaf | Saf-flower |
| | Pre 4 | 100 | 100 | 100 | — | 50 | 99 | 40 | 100 | 95 | 100 | — | 100 | — |
| | Post 2 | 95 | 50 | 99 | — | 20 | 30 | 95 | 100 | 100 | 100 | — | 100 | — |
| | Post 4 | 99 | 60 | 99 | — | 40 | 50 | 100 | 100 | 100 | 100 | — | 100 | — |
| 5. | Pre 2 | 95 | 99 | 100 | — | 10 | 95 | — | 100 | 99 | 100 | — | 100 | — |
| | Pre 4 | 99 | 100 | 100 | — | 30 | 99 | — | 100 | 99 | 99 | — | 100 | — |
| | Post 2 | 10 | 90 | 70 | — | 0 | 30 | 20 | 90 | 100 | 80 | — | 100 | — |
| | Post 4 | 40 | 100 | 95 | — | 0 | 95 | 90 | 100 | 100 | 100 | — | 100 | — |

Greenhouse Weed Control Data. Results Obtained Two Weeks After Treatment.
Rating Scale:
0 = no weed control
100 = complete weed control Many variations of this invention are possible without departing from the spirit or scope thereof.

We claim:

1. A compound of the formula:

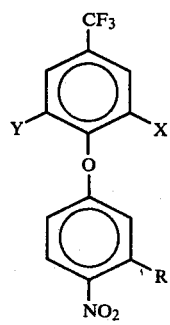

wherein
X is a hydrogen atom, a halogen atom, a trihalomethyl group, a ($C_1$-$C_4$) alkyl group, or a cyano group;
Y is a hydrogen atom or a halogen atom;
R is a COR' group; and
R' is ($C_1$-$C_4$) alkyl.

2. A compound according to claim 1 wherein
X is a hydrogen atom, a bromine, chlorine or fluorine atom, a trifluoromethyl group, a ($C_1$-$C_4$) alkyl group, or a cyano group;
Y is a hydrogen or a bromine, chlorine or fluorine atom;
R is a COR' group; and
R' is a methyl group or an ethyl group.

3. A compound according to claim 2 wherein X is a hydrogen atom or a fluorine or chlorine atom.

4. A compound according to claim 3 of the formula:

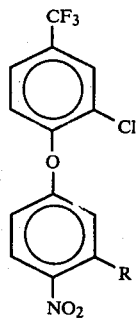

wherein
R is COR'; and
R' is a methyl group or an ethyl group.

5. A compound according to claim 4 of the formula:

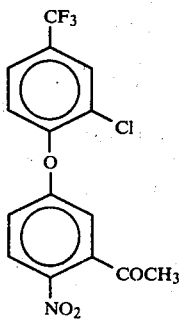

6. A compound according to claim 4 of the formula:

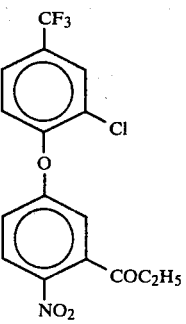

7. A herbicidal composition comprising a herbicidally effective amount of a compound according to claim 1, 2, 3, 4, 5, or 6 in an agronomically acceptable carrier.

8. The composition according to claim 7 which also comprises a surfactant.

9. A method of controlling weeds which comprises applying to a growth medium, prior to the emergence of the weeds from the growth medium, a compound according to claim 1, 2, 3, 4, 5 or 6 in an amount sufficient to control the growth of weeds.

10. The method of claim 9 wherein the compound is applied at a rate of about 0.1 to about 12 lbs./acre.

11. A method of controlling weeds which comprises applying to a growth medium containing weed seedlings a compound according to claim 1, 2, 3, 4, 5 or 6 in an amount sufficient to control the growth of the seedlings.

12. The method of claim 11 wherein the compound is applied at a rate of from about 0.1 to about 12 lbs./acre.

13. A method of controlling undesirable plant growth which comprises applying to the area to be controlled a growth regulating amount of a herbicidal composition of claim 7.

14. A method of controlling weeds in an agronomic crop which comprises incorporating into the growth medium prior to planting the crop and prior to the emergence of the weeds from the growth medium, a compound according to claim 1 in an amount sufficient to control the growth of the weeds.

15. The method of claim 14 wherein the compound is incorporated at a rate of about 0.1 to about 12 lbs./acre.

* * * * *